(12) United States Patent
Katayama

(10) Patent No.: US 7,935,311 B2
(45) Date of Patent: May 3, 2011

(54) AIR PURIFIER, AIR PURIFYING METHOD, FORMED PHOTOCATALYST-SUPPORTING MEMBER AND METHOD OF MAKING FORMED PHOTOCATALYST-SUPPORTING MEMBER

(75) Inventor: Iseo Katayama, Osaka (JP)

(73) Assignee: Jet Company Ltd., Sakai-shi (JP)

( * ) Notice: Subject to any disclaimer, the term of this patent is extended or adjusted under 35 U.S.C. 154(b) by 864 days.

(21) Appl. No.: 11/658,355

(22) PCT Filed: Jul. 25, 2005

(86) PCT No.: PCT/JP2005/013552
§ 371 (c)(1),
(2), (4) Date: Jan. 24, 2007

(87) PCT Pub. No.: WO2006/018949
PCT Pub. Date: Feb. 23, 2006

(65) Prior Publication Data
US 2008/0310993 A1    Dec. 18, 2008

(30) Foreign Application Priority Data
Jul. 26, 2004    (JP) .................................. 2004-217042

(51) Int. Cl.
*A62B 7/08* (2006.01)
*B01J 8/06* (2006.01)
(52) U.S. Cl. ......................... 422/122; 422/120; 422/312

(58) Field of Classification Search .................. 422/122, 422/312, 120
See application file for complete search history.

(56) References Cited

U.S. PATENT DOCUMENTS

| | | | |
|---|---|---|---|
| 5,881,353 A * | 3/1999 | Kamigata et al. | 419/2 |
| 6,063,343 A * | 5/2000 | Say et al. | 422/186.3 |
| 2005/0186124 A1 * | 8/2005 | Fink et al. | 422/121 |

FOREIGN PATENT DOCUMENTS

| | | |
|---|---|---|
| JP | 2000-70355 | 3/2000 |
| JP | 2000-279761 | 10/2000 |
| JP | 3098059 | 9/2003 |

* cited by examiner

*Primary Examiner* — Sean E Conley
*Assistant Examiner* — Kevin C Joyner
(74) *Attorney, Agent, or Firm* — Kratz, Quintos & Hanson, LLP

(57) ABSTRACT

An air purifier according to the present invention includes: a tubular main body 2 having an inner space 3 surrounded by wall portions 6, 7, 8 having a plurality of air movement holes 12, 17; and a light applicator 4 in the inner space for throwing light toward inner surfaces of the wall portions. The inner side of the wall portions exposed to the light is made of a formed porous member. The formed porous member includes an inner surface having a surface part carrying a powdery photocatalyst capable of performing a photocatalytic reaction caused by light. The air purifier allows the carried photocatalyst to perform its catalytic action to a maximum, with a very simple construction.

6 Claims, 7 Drawing Sheets

AIR PURIFIER, AIR PURIFYING METHOD, FORMED PHOTOCATALYST-SUPPORTING MEMBER AND METHOD OF MAKING FORMED PHOTOCATALYST-SUPPORTING MEMBER

TECHNICAL FIELD

The present invention relates to air purifiers, air purifying methods, formed photocatalyst-supporting members used therein and method of manufacturing the formed photocatalyst-supporting members. In particular, the present invention relates to air purifiers, etc. which are capable of making sufficient use of photocatalytic effect with a simple construction.

BACKGROUND ART

It is known that when titanium dioxide is exposed to light, a photocatalytic action takes place and it is possible to sterilize bacteria, etc., and to decompose organic compounds such as odor components, for example.

Without ultraviolet rays, photocatalysts cannot perform sufficient catalytic action. In outdoor environments, sunlight is available. Even in shaded areas, there is a sufficient amount of ultraviolet rays available for catalytic reaction, and a reasonable level of effect can be expected. In indoor environments on the contrary, aside from some sunlight available from windows, light from lighting fixtures such as fluorescent lamps is the only source available, and the light from fluorescent lamps is not enough to obtain sufficient photocatalytic action.

Photocatalysts such as titanium dioxide are marketed in the form of powder. The powder is then mixed with and supported by resin or paper material, and becomes available as filters for example.

As an example, JP-A 2004-44882 (Prior Literature 1) discloses an air purifying apparatus which makes use of the above-described photocatalyst: The photocatalyst is supported on an inner surface of a reactor vessel through which air is passed. The air purifying apparatus is tubular, and includes a fan which moves air from one opening to the other of the tube, and a light source which throw light to the inner surface where the photocatalyst is supported.

Further, JP-A 2000-119995 Gazette (Prior Literature 2) discloses antibacterial paper which includes titanium oxide powder dispersed and bonded uniformly on a surface layer of paper material. In a paper making vat, the titanium is dispersed in the paper material, and then the paper material and the powdery titanium dioxide particles are gathered evenly on a surface of a paper making frame.

According to the air purifying apparatus disclosed in Prior Literature 1, air in the tubular reactor vessel moves only in an axial direction of the tubular vessel. Therefore, only a part of the air which moves through the tubular reactor vessel will pass a proximity to the inner surface where the photocatalyst is supported. In addition, since the photocatalyst is supported only on the inner surface of the tube, the amount of the photocatalyst to act on the air is limited, and therefore it is not possible to expect sufficient air purification effect.

Another problem can be the fan which moves the air. With a small area of surface which supports the photocatalyst, air moving at a high velocity can stay near the photocatalyst only for a small amount of time, making it difficult to provide sufficient air purification effect. Using a fan may also pose noise problems.

According to the antibacterial paper disclosed in Prior Literature 2, it is possible to support titanium dioxide particles reliably, without using a binder. However, because the titanium dioxide particles must be put in a paper making vat so that titanium dioxide is scooped together with the fiber material and supported in the formed sheet during the paper making process, the method requires a large amount of titanium dioxide.

On the other hand, photocatalytic action can be expected only in a range where light can reach, and light is most available on the surface. However, according to the invention disclosed in Prior Literature 2, titanium dioxide is supported uniformly in the direction of depth. Photocatalytic action can only be expected from titanium dioxide which is present in a surface region, and most of the supported titanium particles cannot perform the photocatalytic reactions. This means poor efficiency with respect to the amount of supported photocatalyst.

DISCLOSURE OF THE INVENTION

The present invention provides an air purifier and a formed photocatalyst-supporting member of a very simple construction, capable of allowing a supported photocatalyst to perform a maximum catalytic action.

An air purifier according to claim 1 of the present application includes: a tubular main body having a plurality of air movement holes on a wall portion surrounding an inner space; and a light applicator disposed in the inner space for throwing light toward an inner surface of the wall portion. The wall portion has an inner side made of a formed porous member for exposure to the light, and the formed porous member including an inner surface formed with a plurality of projections and recesses exposable to the light from the light applicator. The formed porous member includes an inner surface having a surface part which supports a powdery photocatalyst for a photocatalytic reaction caused by the light, for air moving through the air movement holes to pass a proximity of the projections and recesses which support the photocatalyst.

According to the present invention, air to be purified comes in and out of the inner space of the tubular main body from a plurality of air movement holes made in the wall portion. The air movement holes may be made anywhere as long as they are made in a wall portion which surrounds the inner space; namely, the holes may be made in any of a circumferential wall portion, an upper wall portion and a lower wall portion. It should be noted here however, that the air movement holes should preferably made at least in the circumferential wall portion or the upper wall portion. The air movement holes made in the wall portions allows outside air to come in and out easily. The air may be moved in and out by using airflow in the room. A forced air movement such as by a fan may also be employed.

Since the air movement holes are made in wall portions of the tubular main body, most of the air that comes in and moves through passes near the surface part of the inner surface of the formed porous member which is the place where the photocatalyst is supported. Meanwhile, according to the air purifier, the inner surface's surface part is exposed to light. Therefore, it is possible to make the photocatalyst work efficiently by moving the air near the surface part.

There is no specific limitation to the shape of the tubular main body. The tubular body may have a circular section or polygonal section. Particularly, by using a tubular shape and by providing a rod-shaped light applicator along the tube's center axis, it becomes possible to throw intense light from a close distance to the entire inner surface of the tubular main body. Further, since it is possible to light a large surface area with a single source of light, it becomes possible to increase air purification efficiency, and to reduce the size of the apparatus. There is no particular limitation to the shape or the number of the air movement holes. Different specifics may be used for the air movement holes depending on the shape, size, etc. of the tubular main body in order to create air flow which will maximize the function of the photocatalyst.

The formed porous member which supports the photocatalyst may be provided only in the area which is exposed to the light. Thus, the formed porous member may be placed inside of a hard outer frame made of a strong material such as metal, or the entire tubular main body may be provided by the formed porous member. Providing the projections and recesses in the inner surface, which is the surface exposed to the light, enables to increase the area that receives the light as well as support an increased amount of the photocatalyst. Further, since air which comes in and out of the air movement holes passes near the projections and recess where the photocatalyst is supported, it is possible to make the photocatalyst work efficiently.

The formed porous member may be provided by molded pulp containing cellulose fiber as a primary component. The formed member made of cellulose fibers has a high rate of porosity and is capable of supporting the powdery photocatalyst in spaces between the fibers. Further, cellulose fibers made from natural material such as pulp have micro-pores in their surfaces which are capable of supporting the powdery photocatalyst. Therefore, it is possible to support the powdery photocatalyst without using or with a very little amount of bonding agents such as a binder. With this arrangement, the surface of each photocatalyst particle is not coated by the binder or the like, enabling to use a high level of photocatalytic action.

Further, the cellulose fiber has a high ultraviolet ray penetration rate. Therefore, light can come not only to a surface but also through a surface part and down to a certain depth from the surface. This allows the photocatalyst supported inside the formed member over a depth range to be hit by the light, which is an advantage that has not been achieved before.

Still further, the invention of the present application provides an air purifier wherein the photocatalyst is supported on a density gradient within a depth range in the inner surface's surface part.

When a formed member made of molded pulp containing cellulose fibers as a primary component is dipped into a liquid carrier such as water in which the powdery photocatalyst is dispersed, capillary action will carry the powdery photocatalyst to a certain depth of the surface part. Also, a greater amount of the powdery photocatalyst is supported at a depth closer to the surface, achieving that the powdery photocatalyst is supported on a density gradient.

The above-described manufacturing method enables to place more amount of the powdery photocatalyst near the surface which is a place where much light is available, as well as to allow the photocatalyst supported inside to be exposed to the light, enabling to use generated light efficiently.

The invention of the present application also provides the air purifier wherein each of the projections and recesses has an outward facing surface having an air movement hole.

By making the air movement hole in an outward facing surface of the projections and recesses, i.e. in the bottom of the inside recess, it becomes possible to let air come in and out near the surface part of the recess. This enables to make the photocatalyst work efficiently on a large amount of air.

There is no particular limitation to the specifics of the projections and recesses. Various different shapes, etc. may be used as long as the area which receives light is increased. For example, the projections and recesses may be provided by an array of outwardly sunken recesses formed in an inner surface of the porous member, with each of the recesses including a bottom having the air movement hole. There is no particular limitation, either, to the specifics of the recesses. For example, the recess may be formed like a bowl or a cup sunken from the inner surface toward an outer side of the tubular main body.

The invention of the present application also provides an air purifier, wherein the circumferential wall portion of the tubular main body is provided by a platy material formed with a repeated pattern of the projections and recesses and bent into a tubular shape. In other words, a platy material which has the air movement holes and the projections and recesses is formed in advance, and then the platy material is bent or rolled into a tube. This enables to form the tubular main body extremely easily.

In the air purifier according to the present invention, a variety of means for moving air may be used. For example, a room fan may be turned on to move air outside of the air purifier and resulting air flow may be utilized. Also, a discharge fan or an intake fan may be provided near the air movement holes so as to move air forcefully.

Further, air warmed by heat from the light applicator or from a heater may be allowed to move upward in the inner space and escape from the air movement holes in an upper portion while air from outside may be allowed to come in the inner space of the tubular main body from the air movement holes in the circumferential wall portion or in a lower portion.

A variety of light sources may be used as the light applicator. Preferably, however, the light source should be capable of generating ultraviolet rays having wavelengths ranging from 300 nm to 400 nm for a high level of catalytic action of the photocatalyst. Particularly, the light source should be a black light which does not emit visible light.

By using heat from the light applicator, air can be introduced into the main body for treatment by the photocatalyst, without any noise. In addition, according to the present invention, air comes into the tubular space through a plurality of air movement holes made in the circumferential wall portion, etc., and moves upward, enabling to treat a large amount of air without depending upon fans.

The invention of the present application relates to an air purifying method which includes: allowing air to come in and out of a tubular main body from a plurality of air movement holes made in the tubular main body having an inside formed with projections and recesses; and allowing the air which comes inside to move near a surface part of the projections and recesses supporting a photocatalyst, while throwing light from a light applicator disposed in an inner space of the tubular main body toward a surface part of the projections and recesses.

Still further, the invention of the present application relates to the air purifying method, wherein air warmed by heat from the light applicator is allowed to move upward in the tubular main body and escape from the air movement holes in an upper portion while air from outside is allowed to come in the inner space from the air movement holes in the circumferential wall portion or in a lower portion.

The invention of the present application also relates to a formed photocatalyst-supporting member provided by a tubular, formed porous member made primarily of a fiber material. The member has an inner space surrounded by a wall portion having a plurality of air movement holes, and a plurality of projections and recesses. The wall portion's inner surface has a surface part supporting a powdery photocatalyst.

According to the formed photocatalyst-supporting member provided by the present invention, it is possible to allow air to come in and out of the air movement holes, to move near the surface part which supports the photocatalyst, and to be treated by the photocatalyst.

The projections and recesses enable to increase the area to be exposed to the light. Further, this increases the amount of the photocatalyst supported. Preferably, the powdery photocatalyst is supported on a density gradient within a predetermined depth range in the surface part. This arrangement allows not only the photocatalyst which is present on the surface but also the photocatalyst which is present inside to perform the photocatalytic action.

Although there is no specific limit to the fiber material to be used, it is preferable to use one which has hydrophilic surface characteristics, since the photocatalyst performs its catalytic action under the presence of moisture. Examples include cellulose fibers and acrylic fibers.

The invention of the present application also relates to a formed photocatalyst-supporting member wherein each of the projections and recesses has an outward facing surface having an air movement hole.

Projections and recesses increase the area for supporting the photocatalyst as well as receiving the light. Therefore, it becomes possible to allow a large amount of photocatalyst to perform the catalytic action, and thus to expect a high level of air purifying effect.

The projections and recesses of the formed photocatalyst supporting member are provided by an array of recesses each including a bottom having the air movement hole. Each recess includes an inner surface having a surface part supporting a powdery photocatalyst.

The formed porous member is provided by molded pulp containing cellulose fiber as a primary component, and the powdery photocatalyst is supported in a surface part of the formed member, in spaces between the fiber material or in micro-pores in the fiber surface.

Supporting the photocatalyst in a sandwiched manner in spaces between the fibers enables to eliminate or drastically reduce the use of a binder or the like. With this arrangement, the surface of photocatalyst particles is no longer coated with the binder components, enabling the photocatalytic action to be performed sufficiently. The surface of cellulose fibers has a multiple number of micro-pores which enables to support the powdery photocatalyst reliably.

Further, cellulose fibers used as the fiber material draws air-borne moisture which helps the photocatalyst to perform its catalytic action sufficiently. Use of pulp molding method enables to form a tubular member which has a high rate of porosity and a high level of strength.

The photocatalyst may be selected from a variety of kinds: For example, the photocatalyst may be provided by those containing titanium dioxide as a primary component. In particular, it is preferable that the titanium dioxide has anatase crystal structure. In addition, a smaller particle size of the powder will increase the surface area of the photocatalyst, increasing a capacity for the photocatalytic reactions. A preferred average particle size for the powdery photocatalyst ranges from 0.1 μm to 0.01 μm.

The invention of the present application is also directed to a method of making a formed photocatalyst-supporting member provided by a formed porous member having a surface part supporting a powdery photocatalyst. The method includes: a forming step of forming a formed porous member having a plurality of projections and recesses; a photocatalyst supporting step of allowing the formed member to absorb, by capillary action from a surface, a liquid carrier containing the powdery photocatalyst dispersed at a predetermined concentration for causing the surface part of the projections and recesses of the formed porous member to support the powdery photocatalyst; and a drying step of allowing the liquid carrier to vaporize for fixing the powdery photocatalyst inside the formed member.

There is no particular limitation to the method of forming the formed porous member. For example, a woven or non-woven cloth made of a thermosetting fiber material may be thermally set into a formed member. Also, a paper making method may be employed, wherein different kinds of fiber materials are gathered into a predetermined frame or mold. For example, pulp molding method may be used.

Various kinds of liquids may be employed as the liquid carrier. Preferably however, the liquid should have a good capillary characteristic matched with the surface characteristics of the fiber material, etc. of which the porous member is formed. Further, the liquid should be removable by evaporation after the powdery photocatalyst has been supported by the porous member. For example, if the porous member is formed of a hydrophilic material such as cellulose fiber, then the liquid carrier can be provided by water. The liquid carrier can be applied to the surface of formed porous member by spraying, dipping, etc.

The air purifier according to the present invention is an efficient air purifying apparatus of a very simple construction offered by: a tubular main body made of a formed porous member including an inner surface part which supports a photocatalyst and a wall portion which has air movement holes and surrounds an inner space for allowing air to come in and out of the inner space, so that the inner surface part can be exposed to ultraviolet rays.

Further, the air purifier according to the present invention has an extremely simple apparatus configuration, which enables to manufacture the apparatus easily and at a low cost.

BEST MODE FOR CARRYING OUT THE INVENTION

Figure 1:
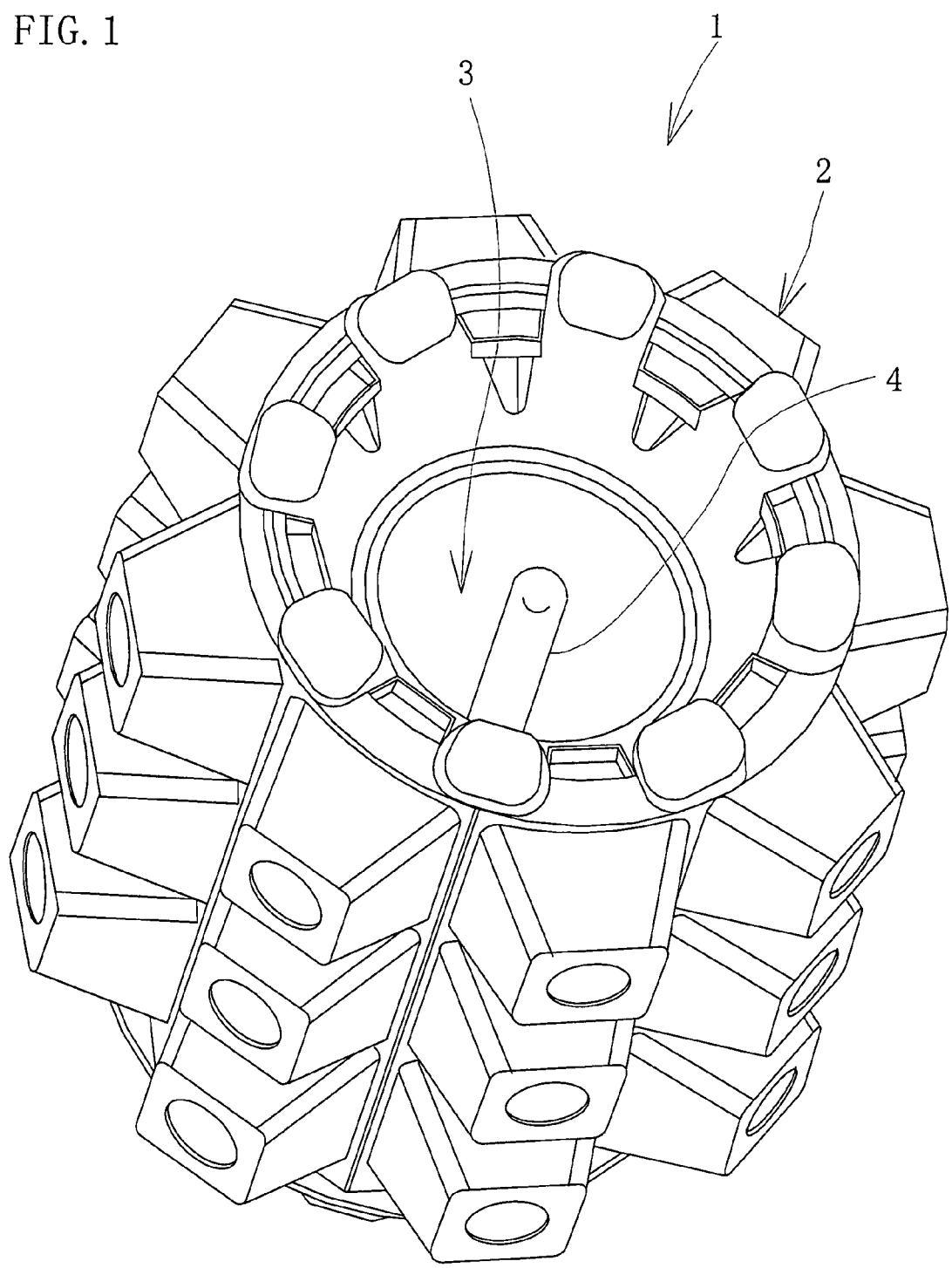
FIG. 1 is a perspective outside view of an air purifier according to an embodiment of the present invention.
Figure 2:
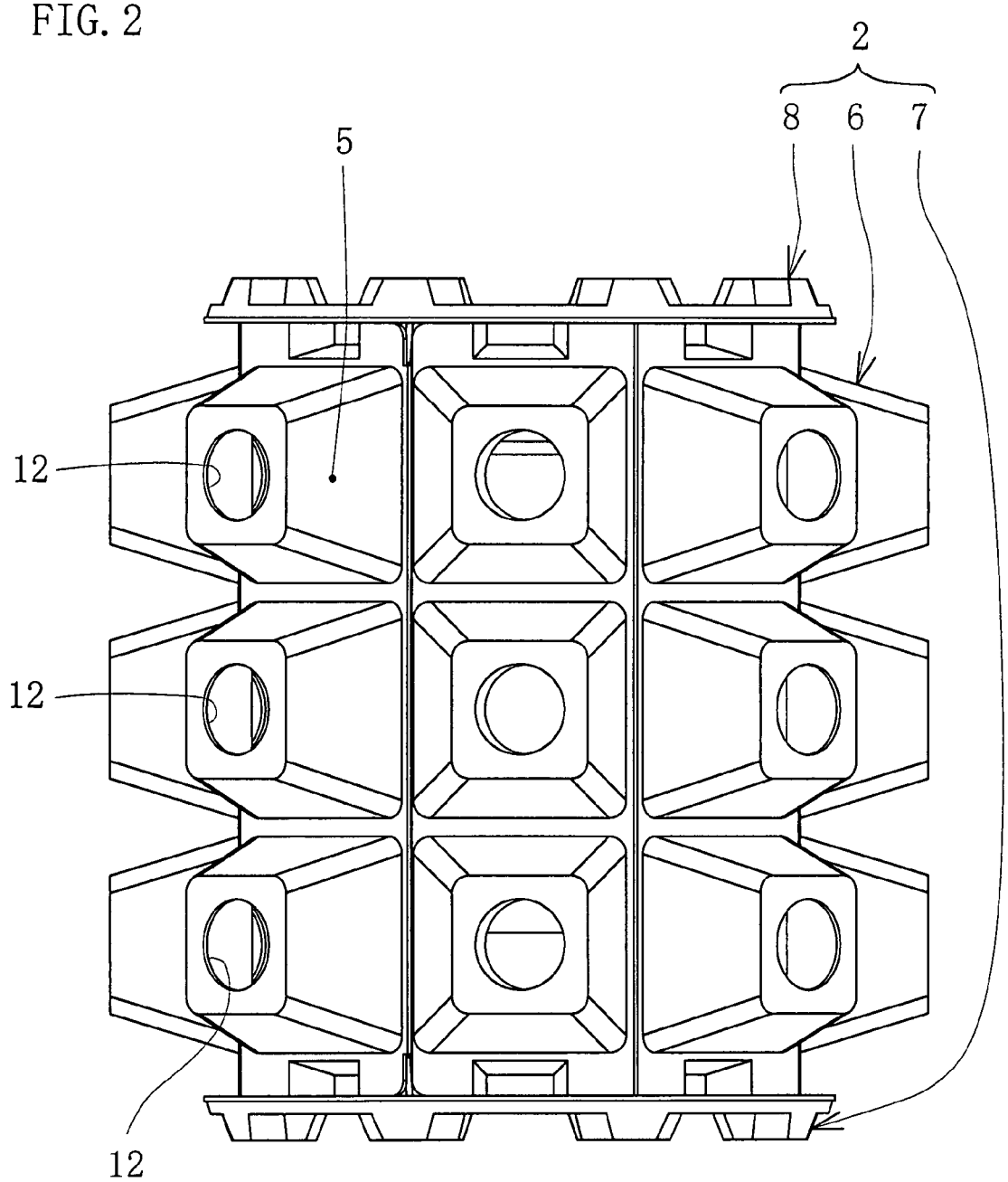
FIG. 2 is a front view of the air purifier in FIG. 1.

FIG. 1 is an overall perspective view of an air purifier according to the present invention. FIG. 2 is a front view thereof. As shown in these figures, an air purifier 1 according to the present invention includes a tubular main body 2 and a light applicator 4 placed in an inner space 3 of the tubular main body 2 for application of ultraviolet rays.

Figure 3:
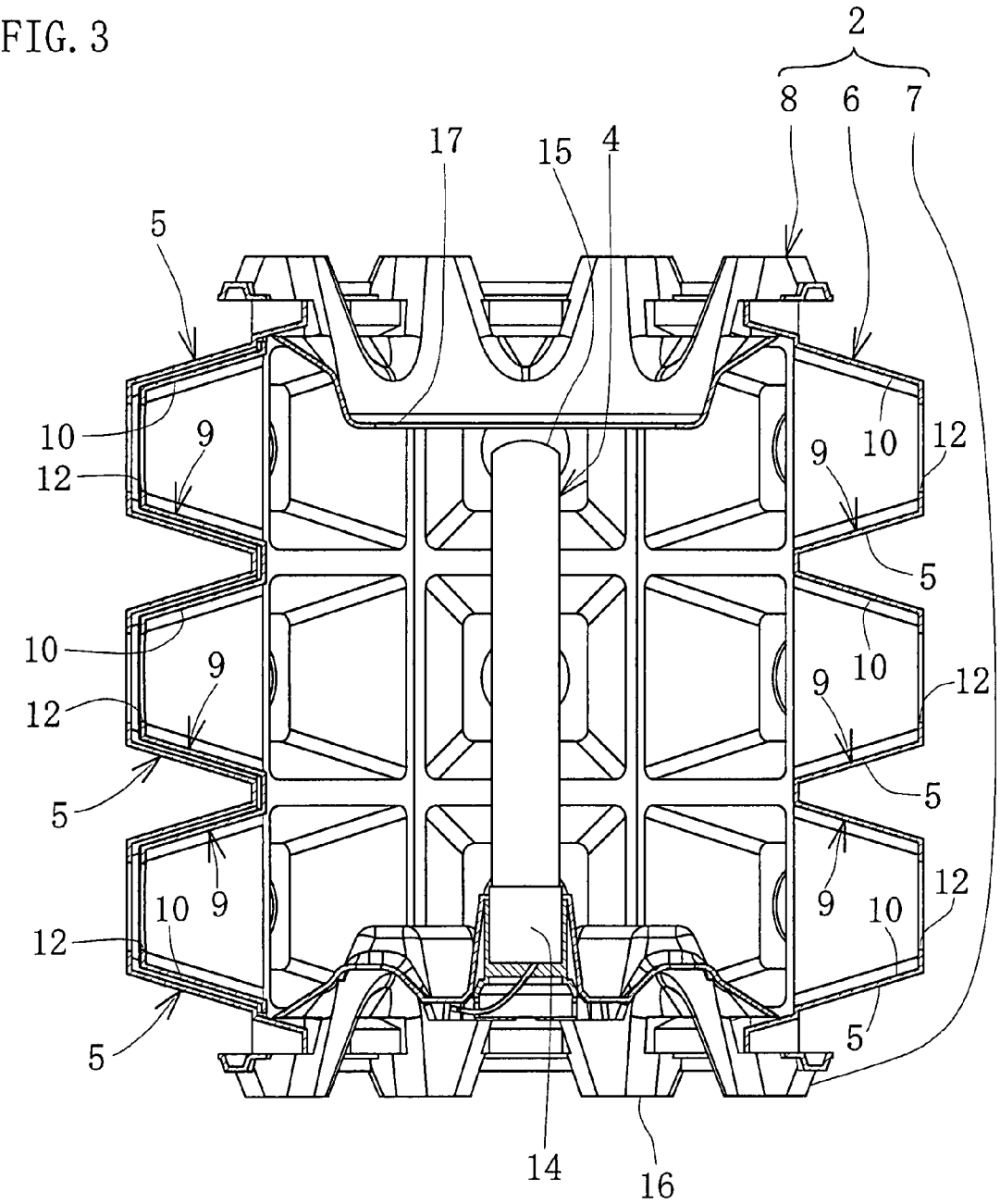
FIG. 3 is an axial sectional view of the air purifier in FIG. 1.

As shown in FIG. 2 and FIG. 3, the tubular main body 2 includes: a circumferential wall portion 6 formed with rows of projections 5 protruding radially outward; a base member 7 connected with a lower edge of the circumferential wall portion 6; and an annular upper member 8 connected with an upper edge of the circumferential wall portion 6.

Figure 5:
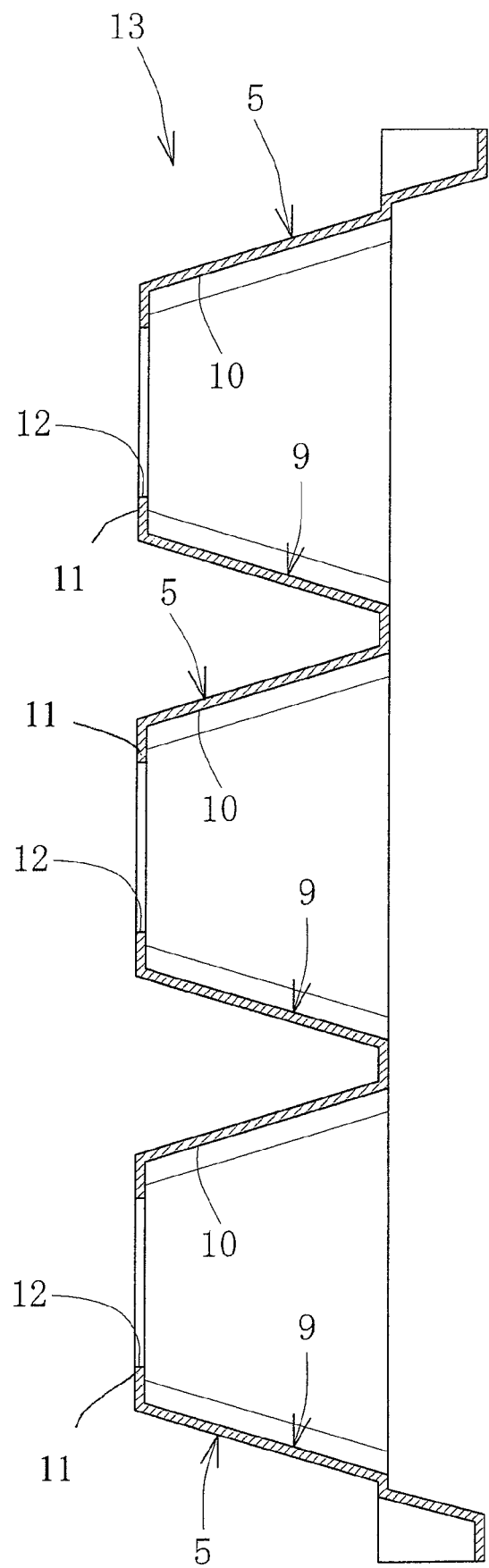
FIG. 5 is a sectional view taken in lines V-V in FIG. 4.

As shown in FIG. 5, inside of each projection 5 is a recess 9 which has an inner surface 10 shaped substantially to a frustum of quadrangular pyramid. Shapes and other factors of the projections 5 and recesses 9 are designed so as to expose the inner surfaces 10 to the light from the light applicator 4. The recesses 9 make a dramatic increase in the area of light reception surface which receives the light from the light applicator 4. Note that in the present embodiment, the projections 5 are formed to have a uniform thickness, to give essentially the same shape to the recesses 9; however, the outer shape of the projections 5 may be different from the inner shape of the recess 9. Each of the recesses 9 include a bottom wall 11 at the terminus of the projection 5 (FIG. 5) which has a circular air movement hole 12 formed therein.

Figure 4:
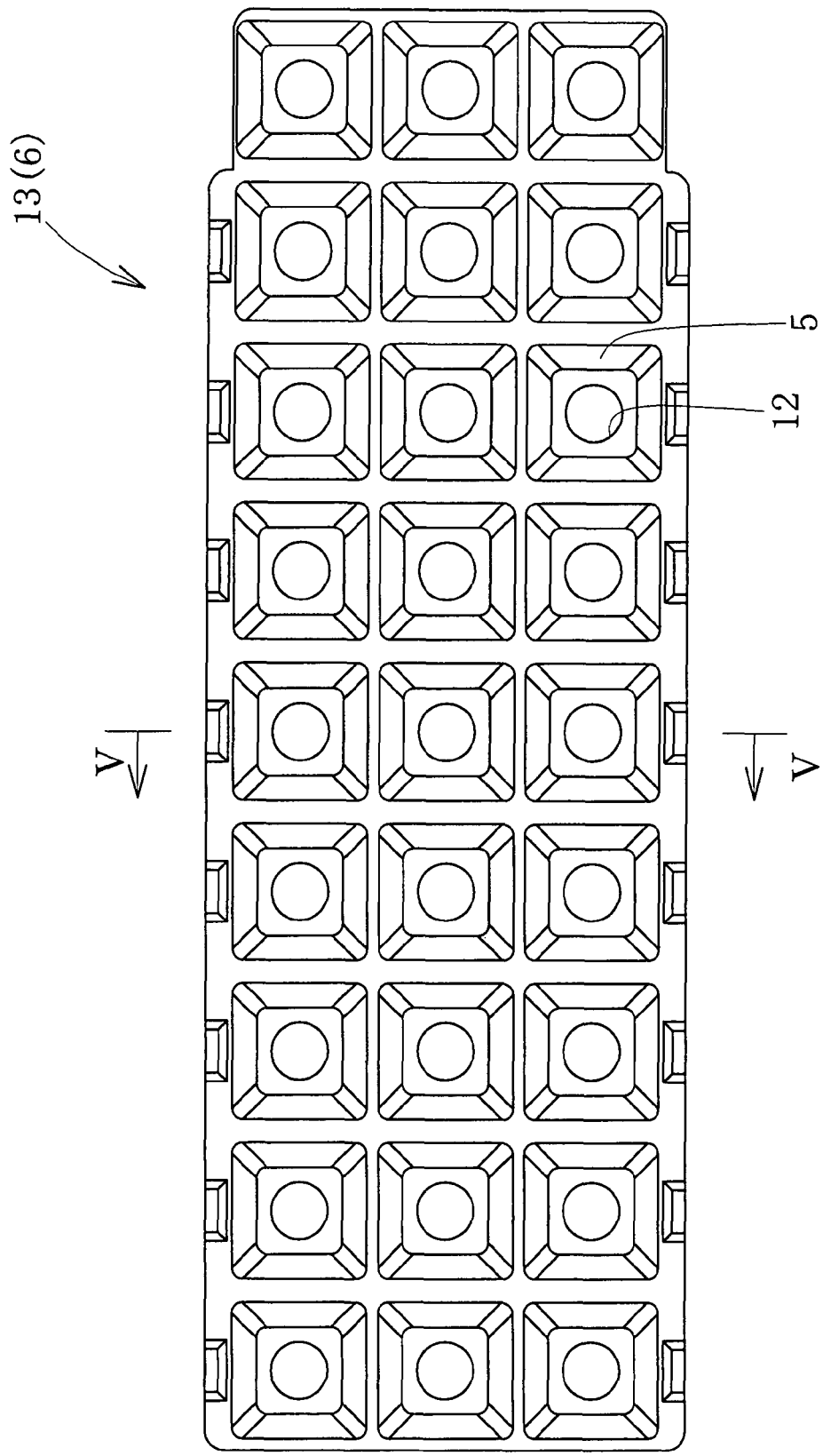
FIG. 4 is a view of a platy member as a component for a circumferential wall portion of the air purifier in FIG. 1.
Figure 6:
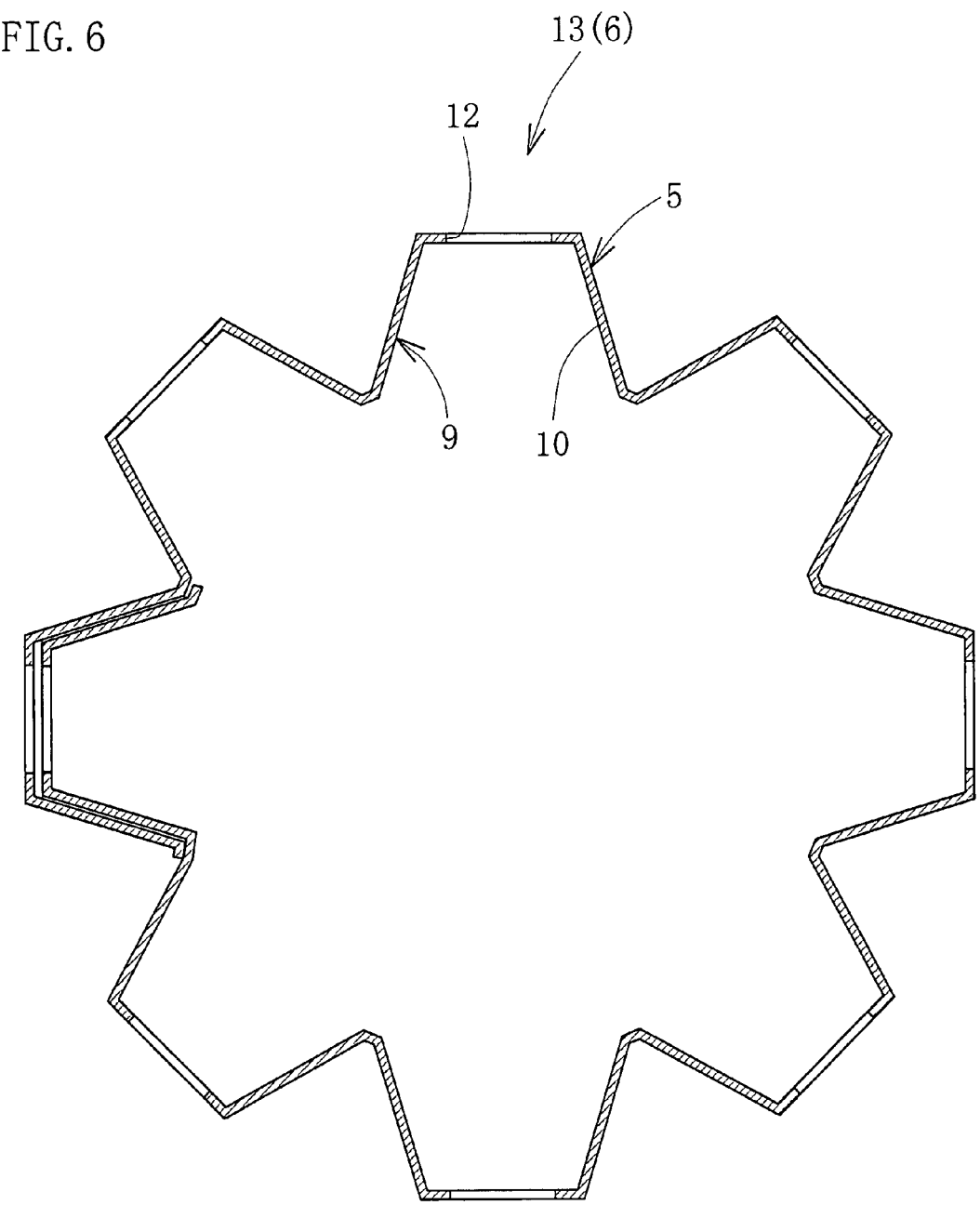
FIG. 6 is a sectional view of the platy member in FIG. 4 bent into a tubular shape.

The circumferential wall portion 6 according to the present embodiment is formed by bending a platy member 13 in FIG. 4 substantially into an octagonal tube as shown in FIG. 6. The platy member 13 is made of a fiber material which contains cellulose as a principal component and is formed as a single piece which has a thickness of 2 mm approx. by pulp molding method. The platy member 13 is formed with rows of the projections 5 and recesses 9 with the air movement holes 12. The octagonal tube of circumferential wall portion 6 is formed by placing the row of projections 5 and recesses 9 on one longitudinal edge onto another row on the other longitudinal edge.

The base member 7 is substantially disc-like and has a circumferential edge fitted into a lower edge of the circumferential wall portion 6. A socket 14 is provided at a center in an inner surface of the base member 7. The socket 14 and the ultraviolet lamp 15 connected therewith constitute the light applicator 4. It should be noted here that in the present embodiment, the base member 7 also has unillustrated small air movement holes to allow air movement. The ultraviolet lamp 15 stands along a center axis of the tubular main body 2. The base member 7 has a lower portion formed with a plurality of legs 16 serving as a stand for the tubular main body. The base member 7 is also a single piece made of the same pulp molding material.

The light applicator 4 is not limited to the one described above; whatever configuration may be used as long as ultraviolet rays are applied at least to the inner surface of the tubular main body 2. Preferably, a black light which is capable of generating ultraviolet rays having wavelengths ranging from 300 nm to 400 nm without including visible light should be used for titanium dioxide to perform the catalytic action.

The upper member 8 is substantially annular, and as shown in FIG. 1 and FIG. 2, includes an outer circumferential edge fitted into an upper edge of the circumferential wall portion 6, and a center portion having an upper air-movement hole 17 which is larger than the air movement hole 12 in the circumferential wall portion 6.

The cellulose fiber material may be provided by a variety of row materials. Examples include virgin pulp materials and used paper materials.

In the present embodiment, the upper member 8, the circumferential wall portion 6 and the base member 7 have their inner surfaces supporting titanium dioxide in the form of powder. In the present embodiment, titanium dioxide has an average particle size of 0.01 through 0.05 $\mu$m. Preferably, titanium dioxide should have anatase crystal structure. Although there is no specific limitation to the specific surface area for titanium dioxide, a preferred range is 50 through 300 square meters per gram. A small amount of binder may be used in order to fix the powdery titanium dioxide to the fiber. It is preferred, however, that the powdery catalyst is supported in the porous material without using binders. If used, the binder may be resin, or may include clay components.

In the air purifier 1 which has the constitution as described above, when the light applicator 4 is turned ON, ultraviolet rays are thrown to inner surfaces of the upper member 8, the circumferential wall portion 6 and the base member 7, enabling to purify air which moves near the inner surface's surface part by photocatalytic effect. Particularly in the present embodiment, a large number of air movement holes made in the entire walls of the tubular main body 2 enable to allow air into the tubular main body for purification, simply by moving the air in the room with a room fan, a ventilating fan, and so on.

The light applicator 4 is provided at a center of the inner space 3, axially of the tubular main body 2. As the light applicator 4 warms up air inside the tubular main body, the large air movement hole 17 in the upper member 8 gives way to an updraft in the inner space 3 even if there is no air movement outside. The updraft enables the air to move out of the inner space 3 through the air movement hole 17 of the upper member 8 while introducing air from outside into the inner space 3 through the air movement holes made in the circumferential wall portion 6 and in the base member 7. Therefore, it is possible to let the purifying function work even if there is no air movement.

In the present embodiment, the powdery titanium oxide is held between fibers of the material in a surface part of each component which constitutes the tubular main body 2, without using a binder or the like. Therefore, surface of the powdery titanium dioxide is not covered by the binder or the like, allowing the photocatalyst to work efficiently on the air passing near the surface part.

Next, description will cover a step of having powdery titanium dioxide supported by a platy material 13 of which the circumferential wall portion 6 according to the present embodiment is made.

In this photocatalyst supporting step, powdery titanium dioxide dispersed in a liquid carrier is sprayed to the inner surfaces of the platy material 13, the base member 7 and the upper member 8. In the present embodiment, water is used as the carrier. Powdery titanium dioxide is dispersed at a 3 through 8 volume percent and sprayed to the surface of the platy member 13, causing the member to support approximately 0.7 grams of titanium dioxide per 100 square centimeters. Then, the platy material 13 is dried outside or in a dryer to remove the liquid carrier. Thereafter, the circumferential wall portion 6, the base member 7 and the upper member 8 are assembled into a tubular main body 2.

In the present invention, the powdery titanium dioxide is not supported with a binder on the fibers but instead, water which serves as the carrier liquid carries the powdery titanium dioxide into spaces between cellulose fibers or into micro-pores in the fibers as the water is absorbed by capillary action into those spaces between the fibers or into micro-pores in the fibers. This enables to cause the surface part of the circumferential wall portion 6 to support powdery titanium oxide without using any binder or the like, or with a very small amount of it.

Figure 7:
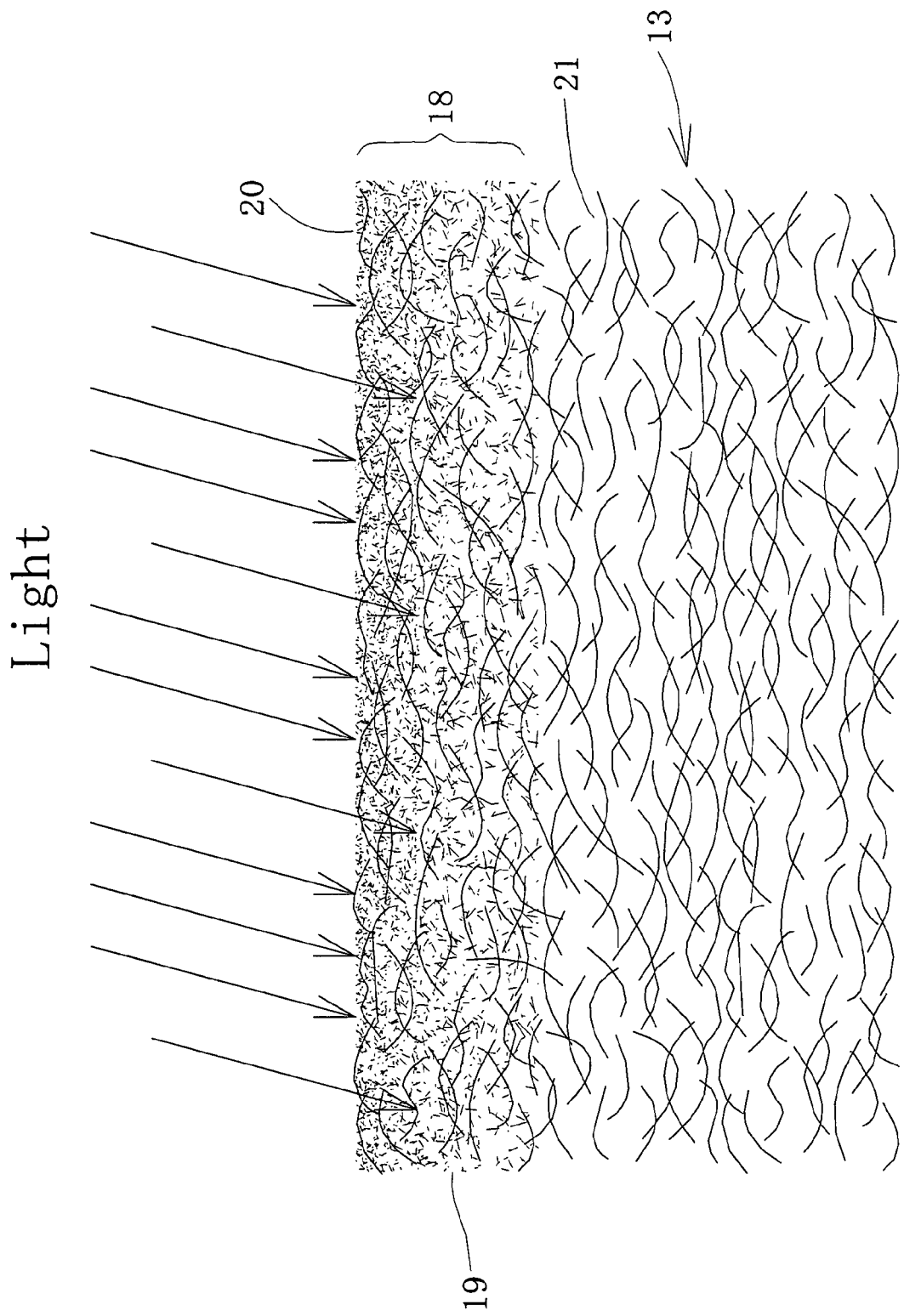
FIG. 7 is an illustration to show a structure and function of a surface part of an inner surface of the air purifier.

FIG. 7 is an illustration showing a structure and function of a surface part 18 of the platy material 13 which supports titanium dioxide 19, according to the present embodiment. As shown in the figure, the powdery titanium dioxide 19 is supported within a certain thickness of the platy material 13 starting from the surface and down to a certain depth, i.e. in the surface part 18. The cellulose fiber has a high ultraviolet ray penetration rate, and the platy member 13 has a high rate of porosity. The pores are much larger than the particles of titanium dioxide. Therefore, light from the light applicator 4 reaches not only a surface 20 of the platy member but also a certain depth. The surface part 18 means a range penetrated by the light from the light applicator 4, and can vary depending upon the rate of porosity and so on of the porous material.

Also, in the present embodiment, more titanium dioxide is supported at a depth closer to the surface 20 which is the side that receives more light. This enables efficient treatment of air which flows near the surface part 18. Air flowing along the surface part can come in and get out of the voids in the fibers. Therefore, photocatalytic action by the titanium dioxide supported in the range penetrable by the light can also be utilized. As a result, efficient purification of the air which moves in the inner space is possible.

Further, in the present invention, titanium dioxide is supported in inner surfaces of the components 6, 7, 8 which constitute the tubular main body 2. This eliminates chances for users' fingers or hands to touch the catalyst. The largest amount of titanium dioxide is supported by the surface part of the recesses 9 formed in the circumferential wall portion 6. Therefore, there is no chance for the powdery titanium dioxide to come off the surface part in normal use.

Next, description will cover results of tests conducted to a formed, porous photocatalyst-supporting member which was manufactured by using the above-described method to see its effect on deodorizing/gas adsorption effect.

Performance Test 1

All performance tests were conducted in a constant temperature and humidity chamber at a temperature of 20° C. and a relative humidity of 65%.

(1) Sample Preparation

Sample pieces each having a size of 50 mm×50 mm were left in the constant temperature and humidity chamber for a period longer than 24 hours.

(2) Preparation of Acetaldehyde Gas

Four liters of clean air and 500 μL of aqueous acetaldehyde solution were put in a 5-liter Tedlar Bag, and left for 24 hours.

(3) Preliminary Test

Four liters of air and the acetaldehyde gas prepared in step (2) were put in a 5-liter Tedlar Bag. The amount of acetaldehyde gas which would give a gas concentration of 100 ppm in the Tedlar bag in two hours was obtained.

(4) Deodorization Test 1 (with no Ultraviolet Ray Application)

Four liters of clean air and a sample piece were put in a 5-liter Tedlar Bag. After adding acetaldehyde gas by the amount obtained in the preliminary test, the bag was sealed, and placed in a dark box to shield from light. The acetaldehyde gas concentration in the Tedlar Bag was measured with a gas detector tube (manufactured by GASTEC Corporation) in 24 hours.

(5) Deodorization Test 2 (with Ultraviolet Ray Application)

Four liters of clean air and a sample piece were put in a 5-liter Tedlar Bag. After adding acetaldehyde gas by the amount obtained in the preliminary test, the bag was sealed and exposed to ultraviolet rays. The acetaldehyde gas concentration in the Tedlar Bag was measured with a gas detector tube (manufactured by GASTEC Corporation) in 24 hours.

(6) The Test was Repeated Two Times. Table 1 Shows Average Values of the Measurements.

TABLE 1

| Sample Name | Acetaldehyde Concentration (ppm) | |
| --- | --- | --- |
| | Without UV Radiation | With UV Radiation |
| Blank Test | 90 | 60 |
| Titanium Dioxide Sheet | 80 | Smaller than 1 |

(unit of measure: ppm)

The test result confirmed that the formed porous member according to the present embodiment exhibited a high deodorizing effect when exposed to ultraviolet rays.

The invention claimed is:

1. An air purifier comprising:
a tubular main body having a plurality of air movement holes on a circumferential wall portion surrounding an inner space;
an annular upper member having an outer circumferential edge fitted into an upper edge of the circumferential wall portion;
a base member having a circumferential edge fitted into a lower edge of the circumferential wall portion; and
a light applicator disposed in the inner space for throwing light toward an inner surface of the wall portion, upper member and base member;
wherein the wall portion, upper member and base member each have an inner side made of a formed porous member for exposure to the light, the formed porous member including the inner surface formed with a plurality of projections and recesses exposable to the light from the light applicator, the formed porous member including the inner surface having a surface part supporting a powdery photocatalyst for a photocatalytic reaction caused by the light, for air moving through the air movement holes to pass a proximity of the projections and recesses which support the photocatalyst,
wherein, each of the projections and recesses has an outward facing surface having an air movement hole,
wherein the projections and recesses are provided by an array of outwardly sunken recesses formed in the inner surface of the porous member, each of the recesses including a bottom wall at the terminus of the projection having the air movement hole formed therein; and
each recess is formed like a bowl or a cup sunken from the inner surface toward an outer side of the tubular main body.

2. The air purifier according to claim 1, wherein the formed porous member is provided by molded pulp containing cellulose fiber as a primary component.

3. The air purifier according to claim 1, wherein the powdery photocatalyst is supported on a density gradient within a depth range in the inner surface's surface part.

4. The air purifier according to claim 1, wherein, each of the projections and recesses has an outward facing surface having an air movement hole.

5. The air purifier according to claim 4, wherein the circumferential wall portion of the tubular main body is provided by a platy material formed with a repeated pattern of the projections and recesses and bent into a tubular shape.

6. The air purifier according to claim 1, wherein air warmed by heat from the light applicator or from a heater can move upward in the inner space and escape from the air movement holes in an upper portion while air from outside can come in the inner space of the tubular main body from the air movement holes in the circumferential wall portion or in a lower portion.

* * * * *